United States Patent [19]

Tsui

[11] Patent Number: 4,814,614

[45] Date of Patent: Mar. 21, 1989

[54] METHOD FOR CHARACTERIZING OIL-BEARING INCLUSIONS VIA FLUORESCENCE MICROSPECTROPHOTOMETRY

[75] Inventor: Tien-Fung Tsui, Richardson, Tex.

[73] Assignee: Mobil Oil Corporation, New York, N.Y.

[21] Appl. No.: 48,438

[22] Filed: May 11, 1987

[51] Int. Cl.$^4$ .......................... G01V 5/00; G01J 3/28
[52] U.S. Cl. ................................. 250/301; 250/255; 250/461.1
[58] Field of Search .................. 250/301, 255, 459.1, 250/461.1, 253, 458.1; 356/70

[56] References Cited

U.S. PATENT DOCUMENTS 3,899,213  8/1975  Fantasia ............................. 250/301

OTHER PUBLICATIONS

McLimans, "Migration and Maturation of Hydrocarbons-Evidence from Fluid Inclusions", AAPG Bull., 69(2), Feb. 1985, p. 4, (Abstract).

Primary Examiner—Carolyn E. Fields
Attorney, Agent, or Firm—Alexander J. McKillop; Charles J. Speciale; Charles A. Malone

[57] ABSTRACT

An ultraviolet (UV) fluorescence microspectrophotometry process for measuring fluorescence spectra of oils in individual micro-sized inclusions. Interpretation of UV fluorescence of oil inclusions in an unknown sample is made by comparison to fluorescence spectra of oils of known composition. This method is a non-destructive process which allows the quality of oils in the undrilled basin to be determined by analyzing outcrop samples containing oil-bearing inclusions. By comparing the fluorescence properties of inclusion oils and reservoir oils, the history of oil migration in petroleum basins can be reconstructed.

20 Claims, 9 Drawing Sheets

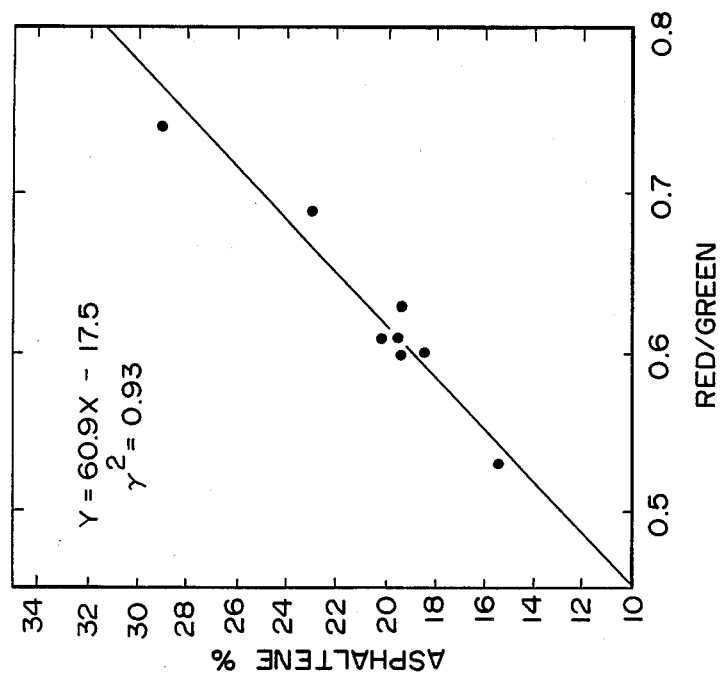
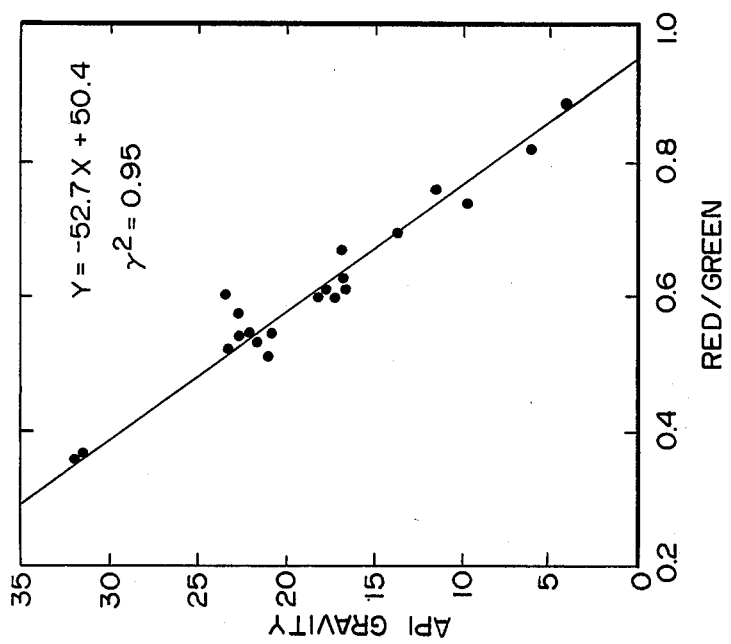

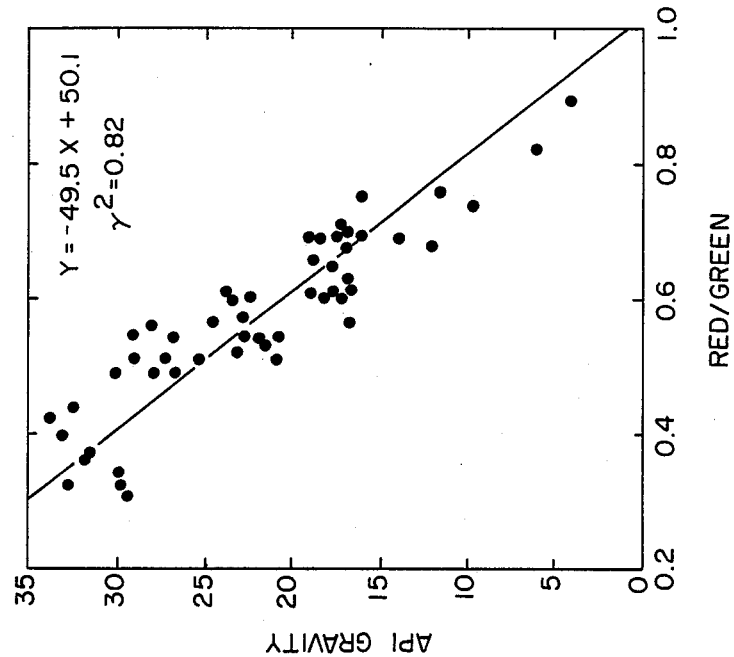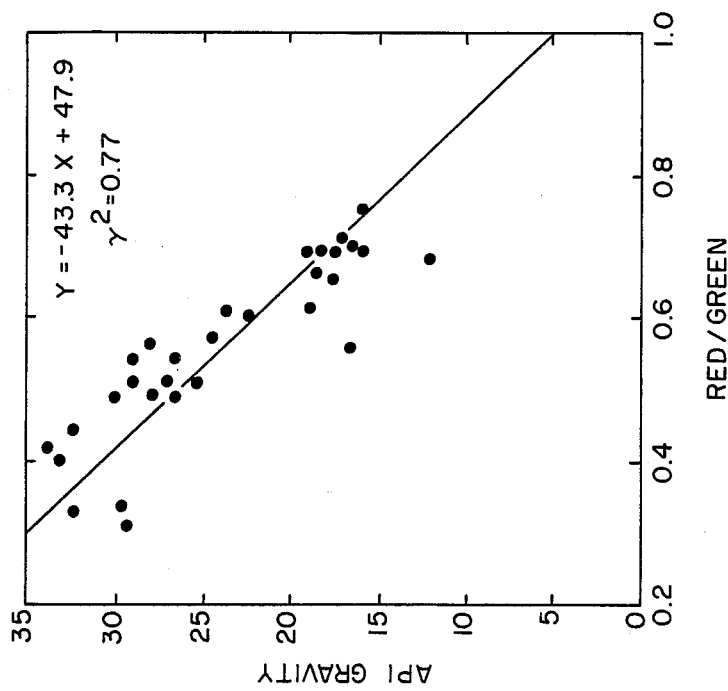

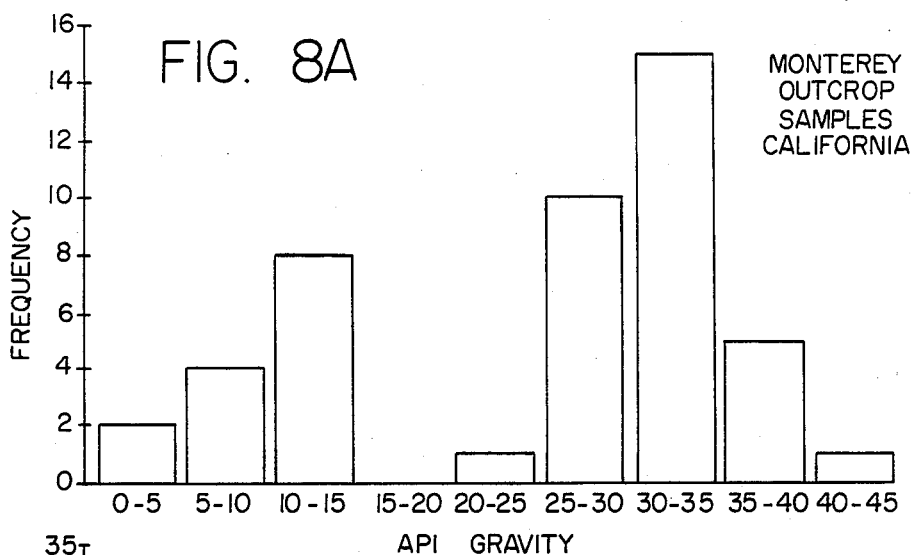
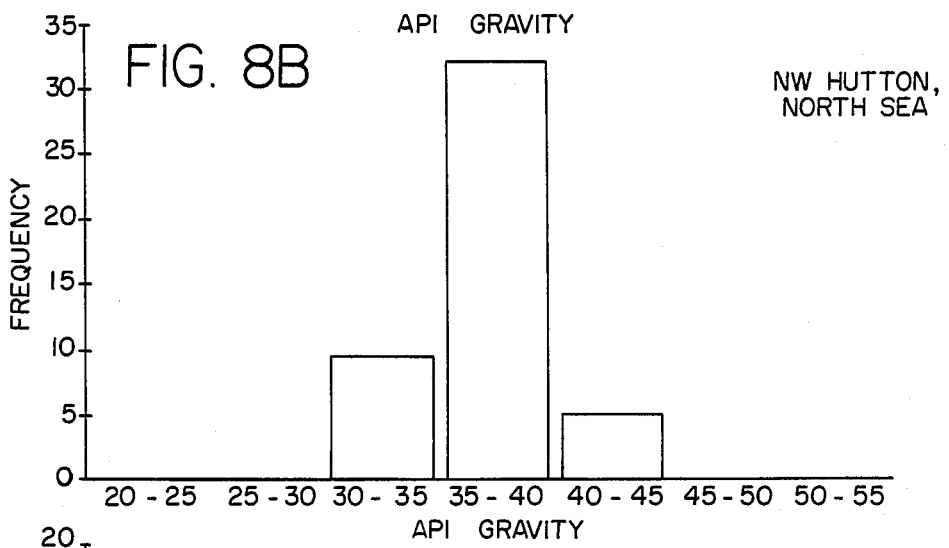
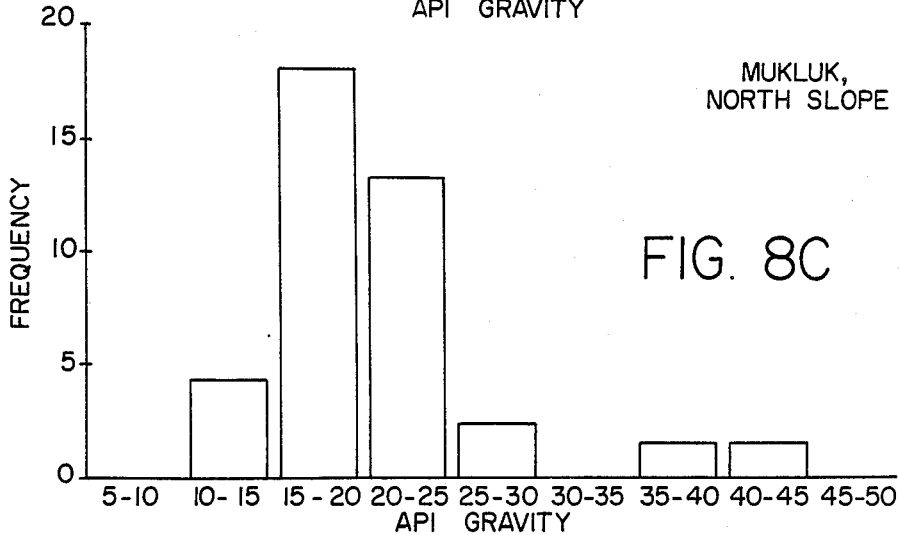

METHOD FOR CHARACTERIZING OIL-BEARING INCLUSIONS VIA FLUORESCENCE MICROSPECTROPHOTOMETRY

FIELD OF THE INVENTION

This invention relates to a method for determining oil quality in undrilled petroleum or areas of new exploration plays where microscopy combined with fluorescence spectrophotometry is utilized.

BACKGROUND OF THE INVENTION

The high detectability of oil fluorescence has frequently been utilized as a means for monitoring oil spills and for prospecting for oil and gas. In drilling for oil and gas, samples of mud, drill cuttings, and cores are often examined under ultraviolet light for evidence of fluorescence due to small quantities of hydrocarbons. This is discussed by R. G. Swanson in a sample examination manual entitled *Methods in Exploration* published by AAPG, (1981). To determine the types and concentrations of oils, several techniques of fluorescence spectrophotometry are available for recording fluorescence spectra of oils (excitation wavelength vs emission wavelength vs fluorescence intensity). Several examples of applications utilizing fluorescence spectrophotometry techniques exist. One use of fluorescence spectrophotometry is for monitoring the source of an oil spill on water. This use is mentioned in U.S. Pat. No. 3,899,213 which issued on Aug. 12, 1975. It is also discussed in an article by A. D. Thruston and R. W. Knight entitled "Characterization of crude and residual-type oils by fluorescence spectroscopy" which appears in *Environ. Sci. & Tech.*, v.5/1, pp. 64–69 (1981).

Another use of fluorescence spectrophotometry is for oil and gas prospecting via remote sensing or near surface sampling methods. A discussion about this use appears in U.S.G.S. *Open-File Report* 84-385, 34 pp (1984) in an article by M. E. Henry and T. J. Donovan entitled "Luminescense properties and chemical composition of crude oils." Fluorescense techniques have also been used for geochemical prospecting. This is discussed by C. F. Hebert in an article entitled "Geochemical prospecting for oil and gas using hydrocarbon fluorescence techniques", *3rd Southern Methodist Univ. Symp. Unconventional Methods in Exploration for Petroleum and Natural Gas. Proc.*, pp. 40–58 (1984).

A third utilization of fluorescence spectrophotometry is for delineating the path of oil migration. This utilization is discussed in an article by R. E. Riecker entitled "Hydrocarbon fluorescence and migration of petroleum" which appeared in *AAPG Bulletin*, v.46/1, pp. 60–75 (1962).

Fluorescence spectrophotometry is used also in evaluating oil-oil and oil-source rock correlations. See "Oil-oil correlations by fluorescence spectrophotometry", *Am. Chem. Soc.* 181st *National Mtg. Abstract,* Division of Geochemistry, paper no 25, by G. G. Janezic et al. (1981). Also see "Applications of total scanning fluorescence to exploration geochemistry", 15th *Offshore Technology Conf. Proc.*, v.3., pp. 393–400, by M. J. Brooks et al., (1983).

The aforementioned fluorescence techniques, however, require a relatively large amount of oil sample (u/cc). To measure the fluorescing characteristics of micro-sized fluorescing matter, a method wherein microscopy is combined with fluorescence spectrophotometry is required. Fluorescence microspectrophotometry is used in the studies of fluorescing organic matter in coals. One study is entitled "Spectral fluorescence measurements of sporinites in reflected light and their applicability for coalification studies" as published in *Petrographic Organique et Potential Petrolier*, CNRS, Paris, pp.49–65 by K. Ottenjann et al. (1975). Another study is entitled "Application of fluorescence microscopy in coal petrology and oil exploration", *Jour. Microscopy,* 109(1), pp. 49–73, M. Teichmüller and M. Wolf (1977). Further use of fluorescence microspectrophotometry in coal studies is disclosed in an article by H. Hagemann and A. Hollerbach entitled "Spectral fluoromatic analysis of extracts - a new method of the determination of the degree of maturity of organic matter in sedimentary rocks, *Bull. Centres Rech. Explor.-Prod.,* Elf-Acquitane, v.5/2, pp. 635–650 (1981). M. Teichmüller and B. Durand have disclosed studies on coals as evidenced in an article entitled "Fluorescence microscopical rank studies on liptinities in peat and coals, and comparison with results of the rock-eval pyrolysis, *Int. Jour. Coal Geo.*, V2, pp. 197–230 (1983).

Fluorescence microspectrophotometry has also been used in the studies of oils trapped as micro-sized inclusions in rocks from sedimentary basins. R. K. McLimans in an article entitled "Migration and maturation of hydrocarbons-evidence from fluid inclusions", *AAPG Bull.,* v.69/2, p. 286 (1985) reported the occurrence of oil-filled inclusions that have different fluorescence spectra in the same crystals. W. Visser in a *Chemical Geology* publication, currently in press, entitled "Oil inclusions in sedimentary rocks", documented the relationship between fluorescence and oil density for a suite of oils from the Maracaibo Basin in Venezula.

To date, no one has sought to combine microscopy and fluorescence spectrophotometry as a means to estimate the oil quality in undrilled petroleum basins or areas of new exploration plays.

SUMMARY OF THE INVENTION

A method is disclosed for determining the characteristics of a micro amount of oil by ultraviolet light (UV) fluorescence microspectrophotometry. In the practice of this method, a sample is obtained from one location which sample contains oil-bearing inclusions. The fluorescence spectra of the oil-bearing inclusions is measured by microspectrophotometry within a desired wavelength range. Thereafter, crude oil samples are obtained from other locations and the fluorescence spectra of each sample is measured by microspectrophotometry using the same wavelength range by which the sample containing oil-bearing inclusions was measured. The quality of the crude oil samples is determined by other scientific methods and the quality of each crude oil sample is correlated to its fluorescence spectra as measured by said microspectrophotometry. Subsequently, the fluorescence spectra of the oil-bearing inclusion sample is compared to the fluorescence spectra of the crude oil samples. By this comparison, the fluorescence spectra of the crude oil sample having a fluorescence spectra closest to the fluorescence spectra of the sample containing the oil-bearing inclusion is ascertained. From this ascertainment, oil quality for oil contained in the oil-bearing inclusion sample is determined.

It is therefore an object of this invention to use UV fluorescence microspectrophotometry as a method for quick determination of the gross geochemical properties of inclusion oils.

It is another object of this invention to correlate the fluorescence characteristics of inclusion and crude oils to their API gravity, aromatic-to-saturate ratios, sulfur, and asphaltene content.

It is yet a further object of this invention to use florescence spectra of inclusion oil as a crude oil maturity indicator.

It a still yet further object of this invention to infer the oil quality of undrilled oil prospects by determining said quality of outcrop samples containing oil-bearing inclusions via use of UV fluorescence microspectrophotometry.

It is a even yet further object of this invention to perform non-destructive, in-situ characterization of fluorescence color of individual oil-bearing inclusions.

BRIEF DESCRIPTION OF THE DRAWING

FIG. 3a shows the relationship between API gravity of Monterey-sourced oils and the oil fluorescence.

FIG. 3b depicts the relationship between oil fluorescence colors and asphaltene content.

FIG. 4a graphically illustrates the fluorescence data and the API gravity of non-Monterey sourced oils.

FIG. 4b represents a composite correlation curve for measurements of Monterey-sourced and non-Monterey sourced oils.

FIG. 8a is a histogram of inclusion oils from Monterey outcrop samples.

FIG. 8b is a histogram of inclusion oils from the North Sea.

FIG. 8c is a histogram of inclusion oils from the North Slope.

DESCRIPTION OF PREFERRED EMBODIMENTS

Figure 1:
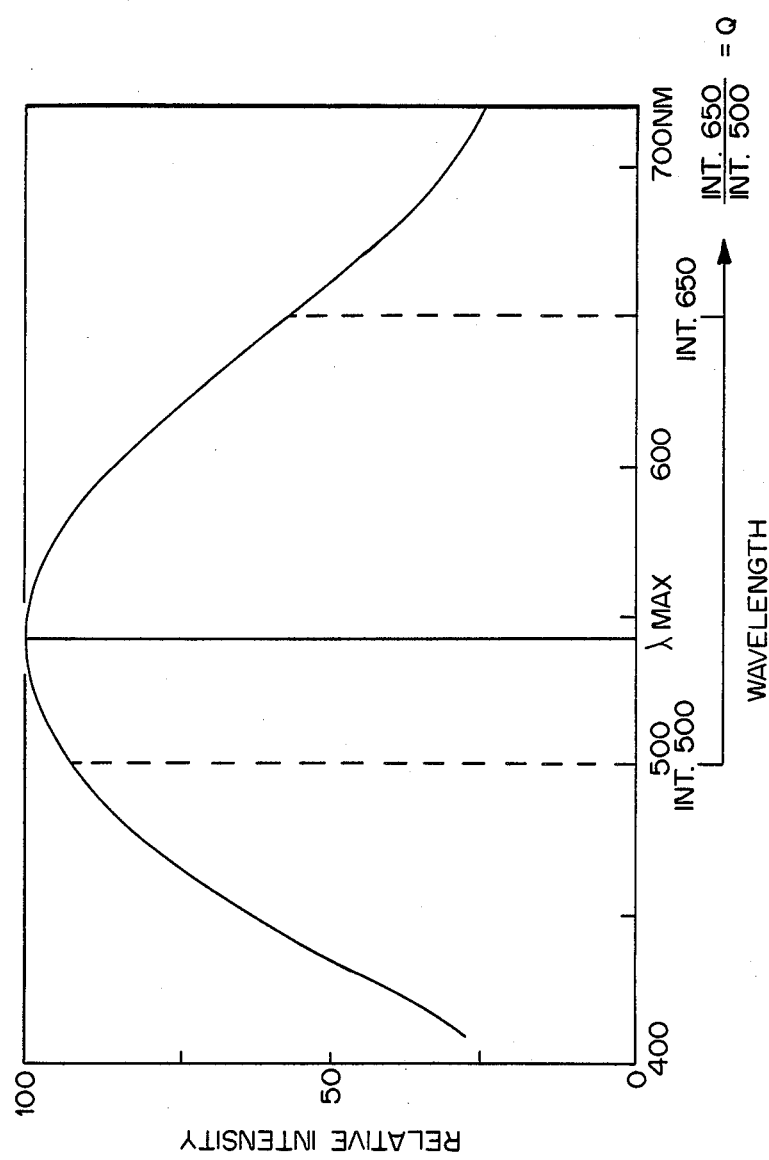
FIG. 1 is a typical spectral curve.

This invention is directed to a method for determining the characteristics of oil trapped as inclusions in rock samples at some distance from the known petroleum reservoirs. These inclusion oils may or may not have derived from the same source rocks as oils in the reservoir. Because outcrop samples containing oil-bearing inclusions are most readily accessible, they provide for quicker evaluations of oil quality in a site remote from well studied basins. Also, samples of drill cuttings or core samples that contain oil-bearing inclusions provide for evaluation of the oil migration history within the drilled basins. These evaluations are made by analyzing samples containing oil-bearing inclusions via ultraviolet light (UV) fluorescence microspectrophotometry.

In the practice of this invention, a sample containing oil-bearing inclusions is obtained. The obtained sample can be derived from rock outcroppings, core samples, and drill cuttings. The oil-bearing inclusions were trapped within the host minerals either during the crystal growth or upon healing of fractures developed within the host minerals after burial. Oil inclusions are micro-samples of the oil and gas generated from contiguous or deeper source rocks and trapped during their migration by the growth or healing of the host crystals. They offer a means to directly examine the nature of the migrated oil. The geochemical properties of the trapped oils can be determined and compared to that of reservoir oils or oils from seeps thereby giving insight about the history of oil migration in sedimentary basins. Where oil-bearing inclusions are identified in areas of new exploration plays, inferences can be made about the quality of oils in the basin. Oil bearing inclusions are generally less than 30 $\mu$m in diameter. Once the sample has been obtained a Leitz microphotometer is used to measure the fluorescence spectra derived from oil-bearing inclusions and crude oil samples. This microphotometer comprises a microscope having a mercury light source, a spectrometer, and a photometer. When UV fluorescence microspectrophotometry is utilized it is possible to perform non-destructive, in-situ characterization of the fluorescence color of individual oil-bearing inclusions. Hydrocarbons fluoresce when they are irradiated by a source of high-energy light (e.g., mercury light). The shade of the fluorescence depends upon the gravity of the crude and the wavelength range of the excitation light source. Under UV light (excitation wavelength between 270–380 nm), the lightest crudes show the palest color, which changes progressively from blue, to white, to yellow, and to dull brown. When the relationships between fluorescence and geochemical properties are established for oils with known composition, the nature of oils within oil-bearing inclusions can be determined through measurement of their fluorescence color. Sample fluorescence is induced by focusing the mercury light source (with excitation wavelength range about 270–380 nm) onto the selected area. The emitted fluorescent light is separated into its component colors upon entering the spectrometer and the intensity at each predetermined wavelength interval is then measured via the photometer.

To calibrate the fluorescence color, crude oils of known composition were first analyzed. To simulate oil-bearing inclusions within natural samples, samples of crude oils were prepared by putting drops of oil in the cavity of a depressed glass slide which is then covered by a glass cover slip. The oil-filled, depressed glass slide was immediately put on the microscope stage for measurement of the fluorescence spectrum to avoid possible alteration due to prolonged air exposure. For the analysis of natural oil-bearing inclusions, a doubly polished plate with thickness of about 80 $\mu$m was prepared. Inclusions were located by focusing into the polished plate.

The fluorescence spectra of crude oils are typically broad and spikeless curves. FIG. 1 is an example of such a spectrum with the relative light intensity plotted against the wavelength interval between 400 and 700 nm. Because of the difficulty in obtaining a universal standard for calibrating the absolute light intensity, relative intensity is usually used in depicting the fluorescence spectra. The parameters commonly used to depict the characteristics of the spectra are the peak maximum and the red-to-green quotient. the peak maximum refers to the wavelength position with the highest intensity. The red-to-green quotient refers to the ratio of the intensity at about 650 nm to that at about 500 nm. As is shown in FIG. 1, the spectrum maximum and red-to-green ratio can be determined from the spectral curve. This spectral curve is the same as the one disclosed by Ottenjann in a 1980 article entitled "Spectral fluorescence microphotometry of coal and oil shale" Leitz Scientific and Technical Information, 7(8), pp.262–273.

In order to interpret the fluorescence of oil-bearing inclusions, relationships between fluorescence and geochemical properties of oils were first established. Three suites of oil samples were selected for measurement of their fluorescence spectra. These suites consisted of oils from California Miocene reservoirs, oils from the Viking Graben, North Sea, and oils from the North Slope, Alaska. Density and composition of these oils were either previously determined or re-measured in preparation for correlation with their fluorescence characteristics.

Twenty-one oils samples known to be sourced from kerogens of the coastal Monterey Formation and thirty-one samples known to be sourced from non-Monterey Miocene kerogens were analyzed for their fluorescence spectra. The Monterey-sourced oil samples came from the fractured Monterey reservoir rocks in the Santa Maria Basin and the western Santa Barbara Channel. Specifically, they were from the S. Elwood Field, with a few selected samples from Jalama, Arguello, Pedernales, Pitas Point, and Hunter Careaga. The non-Monterey-sourced oils were from a number of fields within geographically widely spaced Miocene basins, including the Los Angeles Basin, Ventura Basin, and San Joaquin Valley.

Figure 2:
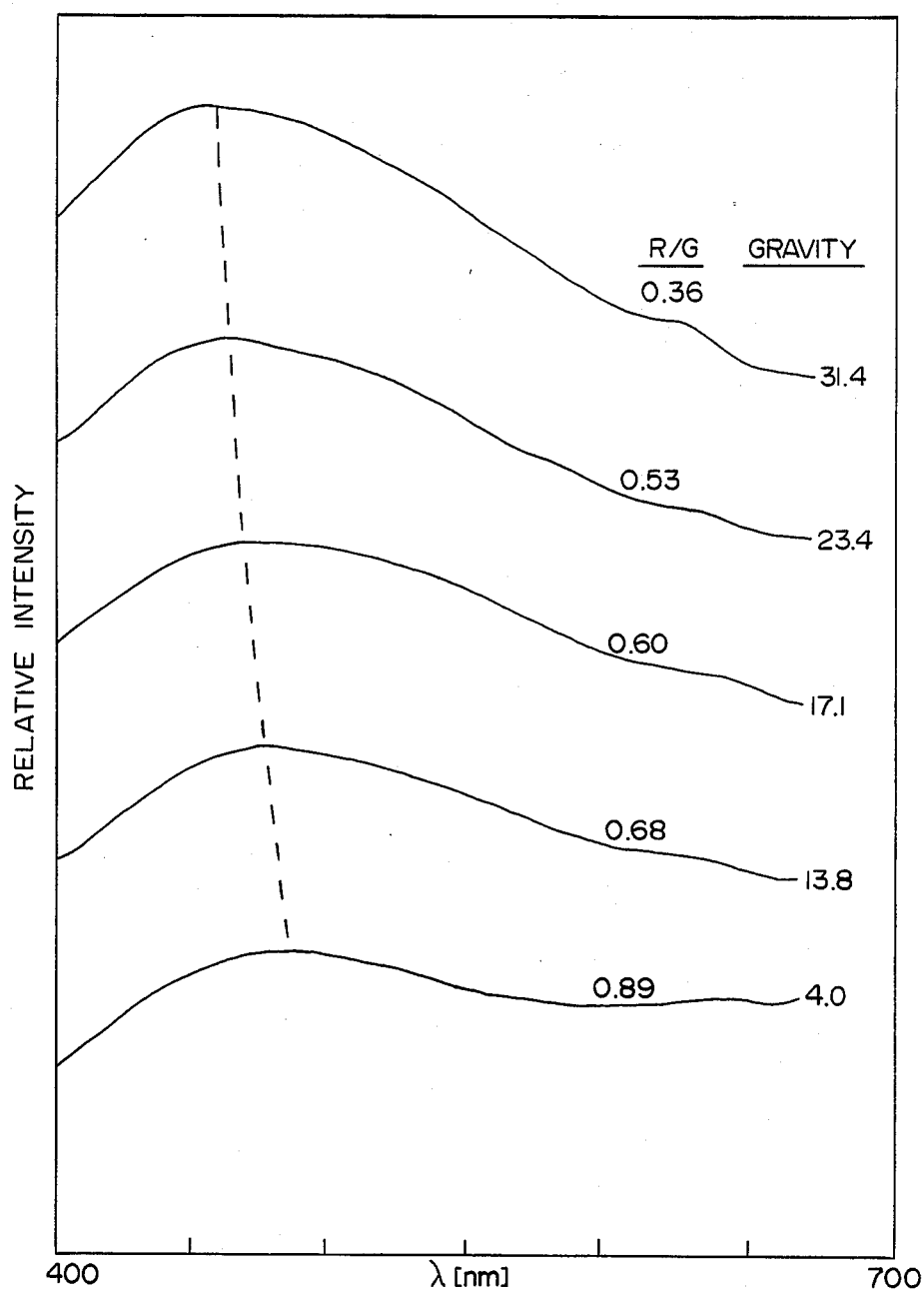
FIG. 2 shows the effect of increasing API gravity relative to fluorescence spectrum.

FIG. 2 shows that with increasing API gravity of oils, the position of peak maximum on the fluorescence spectrum shifts slightly towards shorter wavelength. Low gravity oils exhibit higher fluorescence intensity in orange and red portions of the spectrum, while high gravity oils exhibit higher intensity in the blue and yellow portions. FIG. 3a shows a well defined relationship between the API gravity of Monterey-sourced oils and the oil fluorescence expressed in terms of the red-to-green ratio. A linear regression analysis yields a correlation coefficient of 0.95. A well-defined relationship also exists between oil fluorescence colors and oil asphaltene contents as shown in FIG. 3b, with a correlation coefficient of 0.93. Such excellent correlations are expected among oils generated from the same source rock types. This correlation between asphaltene content and red-to-green ratio for Monterey-sourced oils is depicted in FIG. 3b.

A similar linear relationship exists between the fluorescence data and the API gravity of oils sourced from non-Monterey kerogens as shown in FIG. 4a. The correlation, however, is not as good as that for the Monterey-sourced oils, as evident from the increased scatter of data points. The correlation coefficient is 0.77. There is also a slight difference in the slope of the correlation curve.

The difference in slopes between the fluorescence-API gravity correlation curve for oils sourced from Monterey kerogens and that for oils sourced from non-Monterey Miocene kerogens indicates that no single relationship holds for all California Miocene oils. To use this type of correlation to estimate API gravity of oils trapped in oil-bearing inclusions when the source of inclusion oils cannot be reasonably ascertained, a composite correlation curve, as depicted in FIG. 4b, can be used. This composite curve is based on measurements of Monterey-sourced plus non-Monterey-sourced Miocene oils. Said correlation curve probably yields the best possible estimate of API gravity by averaging out the uncertainties due to the unknown source of inclusion oils. FIG. 4b represents a composite plot of data used in FIG. 3a and 4a.

Figure 5:
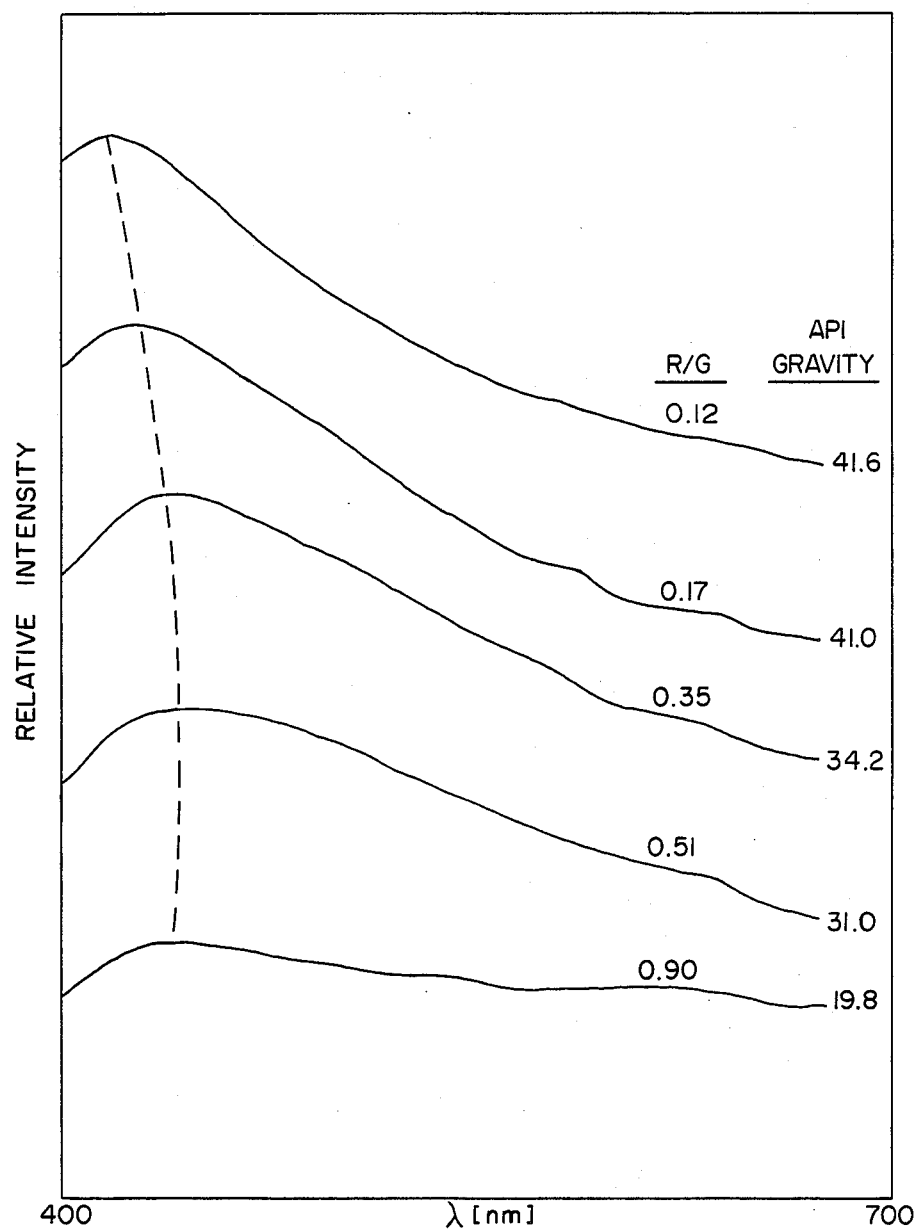
FIG. 5 shows graphically the fluorescence spectra shift with increasing API gravity.

Twenty-two oil samples from various fields in the Viking Graben area of the North Sea were analyzed for their fluorescence spectra. These oils were presumably sourced from the same source rock type—the Kimmeridgean shale of Jurassic age. As is shown in FIG. 5, the fluorescence spectra shifts with increasing API gravity.

Figure 6B:
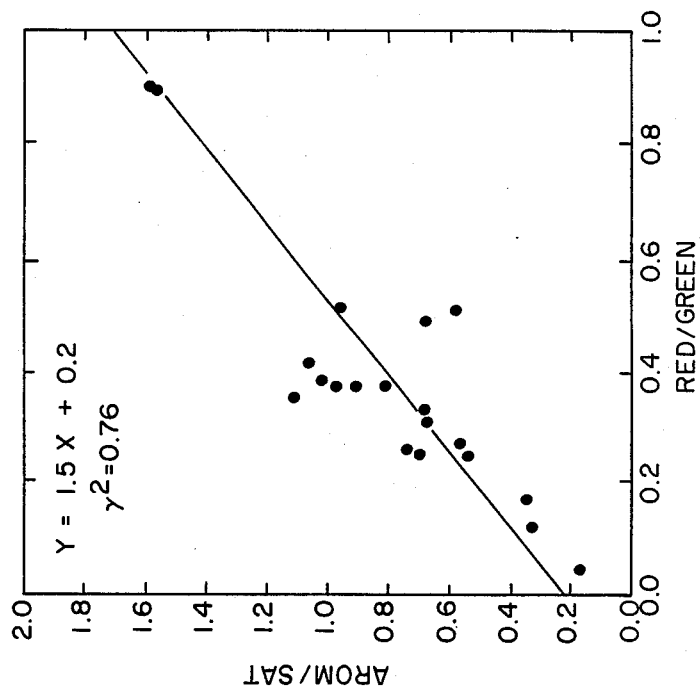
FIG. 6b depicts the aromatic-to-saturate ratio correlation to the red-to-green ratio.
Figure 6A:
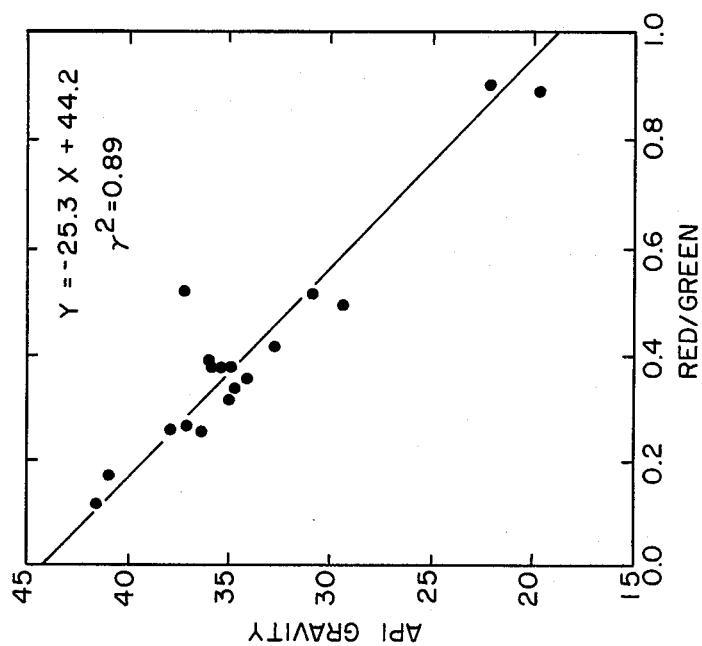
FIG. 6a illustrates graphically the correlation between API gravity and oil fluorescence.

Like the Monterey oils, the fluorescence spectra of North Sea oils display a shift toward shorter wavelength with increasing oil gravity. This is represented in FIG. 5. The correlation coefficient between the API gravity of North Sea oils and their fluorescence expressed in terms of red-to-green ratio is 0.89. This correlation is shown in FIG. 6a. Unlike the asphaltene-rich Monterey-sourced oils that exhibit a fluorescence-asphaltene correlation, the red-to-green ratios of North Sea oils are correlatable to their aromatic-to-saturate ratios. The correlation coefficient is 0.76 and it, along with the aromatic-to-saturate ratios, are depicted in FIG. 6b.

For the studies of Alaskan North Slope oils, selection of oil samples sourced from a single source rock is practically impossible. Seven crude oil types have been identified, with each displaying its own source characteristics. It has also been demonstrated that there is much mixing of oils in the North Slope area. For example, much of the oil produced from the Prudhoe Bay Field is double-sourced, containing various proportions of Cretaceous and Triassic-Jurassic oils. Because of the extent of oil mixing, it is unrealistic to restrict this comparison to only the end member of each oil type. Except oils from the NPRA area, which are distinctly different from oils from the other North Slope fields, oils from the Prudhoe Bay unit, Kuparuk River unit, and a few samples from the Hemi Springs, Milne Point, and Gwydyr Bay units were all included in measurements for their fluorescence spectra.

Figure 7A:
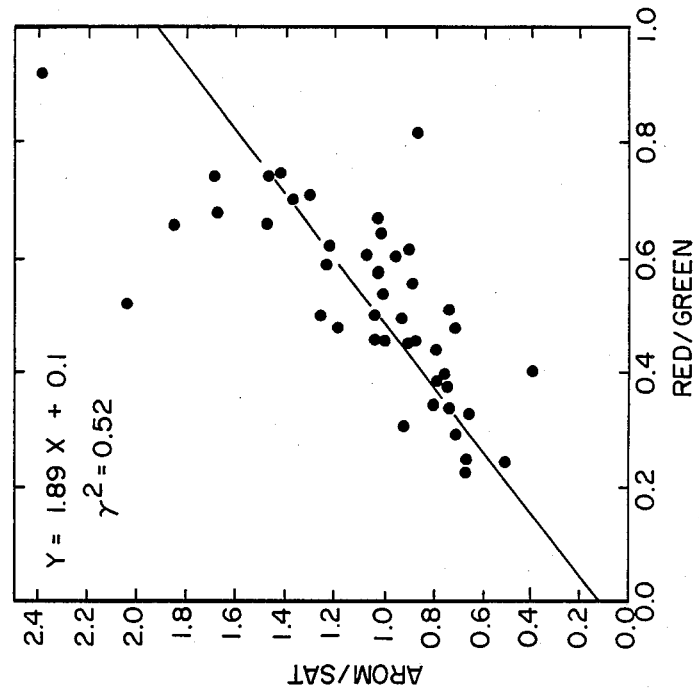
FIG. 7a illustrates graphically the linear relationship between API gravity and the fluorescence of North Slope oils.
Figure 7B:
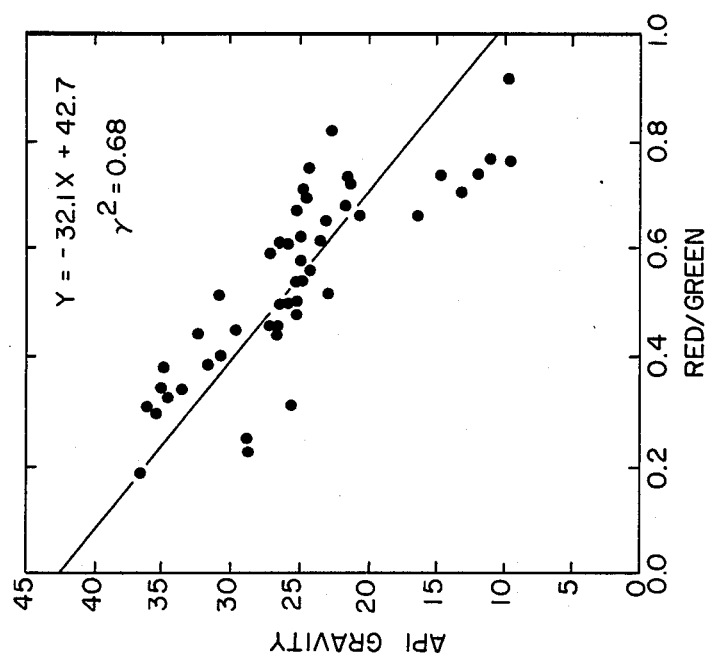
FIG. 7b shows graphically the relationship between the red-to-green ratio and the aromatic-to-saturate ratio of North Slope oils.

FIG. 7a shows that the relationship between API gravity and the fluorescence of North Slope oils is also linear. The data points, however, are much more scattered than those of the California Miocene and north Sea oils, with a correlation coefficient of 0.68. These relationship between the red-to-green ratio and the aromatic-to-saturate ratio is even weaker, with a correlation coefficient of 0.52. This relationship is shown in FIG. 7b. These relatively poor correlations are probably attributable to the extensive mixing of oils sourced from different source rocks in the North Slope.

Crude oils are complex mixtures of many hydrocarbon and non-hydrocarbon molecules, each of which has its own characteristic fluorescence spectrum. The fluorescence spectrum of a whole oil sample is, therefore, the combined result of many narrow but overlapping spectra. This is the reason that the fluorescence spectrum of crude oils typically displays a broad maximum. The fluorescence phenomenon is induced by irradiating a fluorescent substance with UV light. Absorption of UV light results in a direct excitation of the atoms or molecules of the fluorescent substance. As the electrons of the excited atoms or molecules spontaneously revert to their original state or to a lower energy state, a characteristic fluorescent light is emitted.

Aromatic compounds are known to be the major source of oil fluorescence, while saturated hydrocarbons do not fluoresce. It is, however, not possible to identify individual components responsible for the overall fluorescence character. Little is known about the net fluorescence when fluorescence of individual compounds are combined together as in the case of crude oils. However, as shown above, well-defined relationships do exist between net fluorescence and gross geochemical properties of crude oils.

Good correlations between the UV fluorescence and the density of oils are therefore expected. Good correlations exist because oil density is heavily influenced by the proportions and types of heavy hydrocarbon components present in the whole oil, notably the aromatic compounds that are the major contributor to crude oil fluorescence. The effect of overall chemical composition on fluorescence is also reflected in the close correlation between the UV fluorescence and the aromatic-to-saturate ratio. In the case of asphaltene-rich oils (e.g., Monterey-sourced oils), the oil fluorescence is better related to their asphaltene content. This mainly reflects the close correlation between the asphaltene content and oil density in asphaltene-rich oils. the shift in oil fluorescence with decreasing oil density towards lower wavelength is due mainly to the decrease in size of aromatic compounds (in terms of number of fused benzene rings), which is accompanied by a decrease in the concentration of heavy aromatics and heterocompounds relative to that of saturates.

Well-defined fluorescence-API gravity and fluorescence-oil composition relationships exist for oils of the same family that have migrated various distances from the source. As shown in the previous section, the relationship is different for families of oils that have been generated by different types of source rocks. During migration, oil composition is gradually altered through selective removal of the heavier heteroaromatic and aromatic compounds. The consequence is a gradual decrease in the aromatic-to-saturate ratio and a shift of fluorescence color to shorter wavelength. Because aromaticity decreases with increasing maturity of the oil, fluorescence color can be used as a crude indicator of oil maturity.

Because saturated hydrocarbons do not fluoresce, one can dissolve a large amount of natural gas in the oil without changing its fluorescence color. This is discussed in an article by W. Visser now in press and entitled "Oil Inclusions In Sedimentary Rocks" which has been submitted for publication in *Chemical Geology*. The amount of gas in solution can, however, drastically alter the density of oil. The fluorescence spectrum of oil inclusion, therefore, only measures the density of the $C_6+$ fraction of the trapped oil and not the density of the trapped oil with its gas in solution. In essence, the API gravity derived from fluorescence measurements is similar to the conventionally measured API gravity of reservoir oils. The latter is generally a measurement of oil density at surface conditions, at which conditions a large amount of solution gas is lost, irrespective of the original reservoir gas concentrations.

In order to demonstrate that hydrocarbon fluorescence in oil=bearing inclusions was similar to hydrocarbon fluorescence of reservoir oils, samples containing oil-bearing inclusions were needed.

Oil-bearing inclusions occur in outcrop samples of the Monterey Formation in coastal California, in cements from the NW Hutton Field, North Sea, and in quartz overgrowths of the Mukluk well, Alaska. Fluorescence measurements of oil-bearing inclusions from each of these three areas were obtained. The API gravity of the trapped oil in each oil-bearing inclusion wa estimated utilizing the correlations established in the previous section.

Outcrop samples were collected from the Santa Barbara Channel area at Vandenberg-Jalama Beach. These samples are fracture-filling calcite cements with quartz infilling the center of the fracture. Calcite displays distinctive symmetrical growth bands that can be traced from the wall toward the center of fractures. Similar types of fracture-filling samples collected along the nearby coastal areas are tar-filled but are barren of oil-bearing inclusions.

Two distinctively different types of hydrocarbon inclusions are found in the growth bands of calcite. One type is a relatively large, reddish-brown colored inclusion that fluoresces yellow under UV irradiation. The other is a small, clear inclusion type that has a bright, bluish-white fluorescence color. Both yellow-white and bluish-white fluorescing inclusions often outline the growth zones of calcite. Quartz is mainly barren of inclusions, although yellow-fluorescing inclusions occasionally occur as secondary inclusions within healed fractures in quartz.

Fluorescence spectrophotometric analyses show that the API gravities of the yellow-fluorescing inclusion oils cluster around 10°–15° while the API gravities of blue-fluorescing inclusion oils cluster around 30°–35°. The measured density range of inclusion oils reflects the density range of crude oils produced from that area. API gravity of produced oils ranges from near zero (onshore Santa Maria Basin) to as high as 32 degrees (South Elwood, offshore Santa Barbara Channel).

Figure 9:
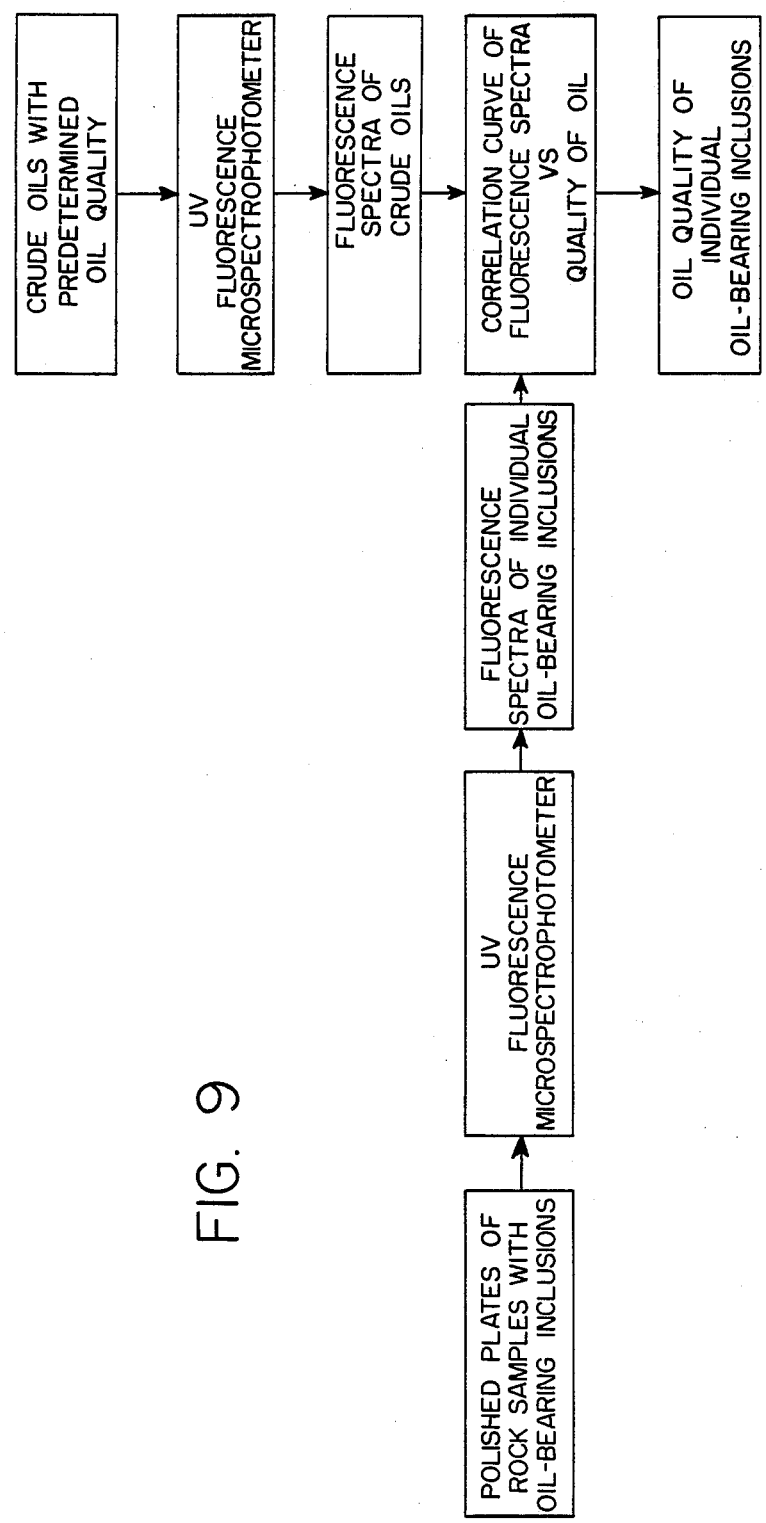
FIG. 9 is a flow diagram illustrating the method.

FIGS. 8a, 8b, and 8c depict histograms showing the frequency of distribution of fluorescence-derived API gravity of inclusion oils from various sample locations. FIG. 8a represents a histogram of Monterey outcrop samples from the Santa Barbara Channel area. FIG. 8b is a similar histogram of the NW Hutton Field from the North Sea. A histogram showing distribution frequencies from the Mukluk test well on Alaska's North Slope is depicted in FIG. 8c. FIG. 9 shows a flow diagram illustrating the method.

Oil quality is a major factor controlling the producibility of reservoirs in the fractured rocks of the Monterey Formation in the Santa Maria Basin onshore, offshore, and in the western Santa Barbara Channel. Investigation has shown that both sulfur and asphaltene contents in Monterey oils are linearly and closely correlated with API gravity. One such investigation has been revealed by W. L. Orr in an article entitled "Kerogen/asphaltene/sulfur relationships in sulfur-rich Monterey oils." This article appears in *Organic Geochemistry*, ed. D. Leythaeuser, v.10,p.499–516, (1986). Measurements such as UV fluorescence that can be used to predict API gravity, therefore, can also be used to set limits on other properties such as sulfur and asphaltene contents, and therefore, could provide information for evaluating the economics of undrilled prospects of new exploration plays in offshore California.

The NW Hutton Field is located in the Viking Graben area of the North Sea. Samples studied were obtained from the Brent Formation at drilled depths between 14,255 and 18,605 feet (true vertical depths between 11,000 and 12,00 feet). This formation includes sandstones which contain several diagenetic phases: quartz, kaolinite, and illite. Quartz appears as euhedral crystals in optical continuity with host grains of detrital quartz. It is at the contact between the authigenic and detrital quartz, as well as within the healed fractures in quartz, that oil-bearing inclusions occur.

Oil-bearing inclusions are colorless to pale yellow in transmitted light and fluoresce yellow in UV irradiation. Fluorescence measurements of the oil-bearing inclusions yield an average red-to-green ratio of about 0.33±0.06. Using the fluorescence-API gravity correlation established for oils from the Viking Graben, the majority of inclusion oils are calculated to have an API gravity between 35°–40° with an average of 36.7°. API gravities of the four reservoir oil samples were 35.4°, 35.0°, 32.8°, and 34.2°. Similarities in the density and the fluorescence spectra between the majority of inclusion oils and the reservoir oil suggest that these two oils have the same or similar source. The inclusion oil and the reservoir oil are likely to be derived from the same migration event. This inclusion oil probably represents the front of a single oil migration episode where thereafter hydrocarbon eventually filled the reservoir and arrested diagenesis.

Oil-bearing inclusions were found in quartz overgrowths and in healed fractures in quartz from the Sadlerochit sands of the Mukluk well. To reconstruct the history of oil migration for this region, it had to be determined whether the inclusion oil is related to the Mukluk drill stem test (DST) oil and to other oils from the North Slope.

The inclusion oils have a clear honey color in transmitted light and fluoresce bright yellow under UV radiation. Fluorescence measurements indicate that the majority of inclusion oils have red-to-green ratios between about 0.55 and 0.86, with an average of about 0.74. Based on the fluorescence-API gravity correlation curve established for the North Slope, these red/green values convert to an API gravity range of about 15°–25°, averaging about 19° as shown in FIG. 8c. This is significantly higher that the 10°–13° API gravity measured for the DST oils. The DST oil shows a dark brown color in transmitted light and barely fluoresces. Geochemical analysis of Mukluk DST oil indicated that it is a crude oil of low maturity and is not biodegraded. Geochemical evidence, however, is inconclusive to eliminate the possibility that Mukluk DST oil had been water washed, which would yield a heavy oil by removing water soluble paraffins and aromatics. The difference in density between the inclusion oil and the DST oil may be attributable to the water washing of an originally lighter oil, probably recorded by Mukluk oil-bearing inclusions. An alternative interpretation invokes two episodes of hydrocarbon migration. An early migration of lighter oil is recorder by the Mukluk oil-bearing inclusions. A later episode of heavy oil is represented by the oil produced from the drill stem test. Quartz overgrowths apparently precipitated between migration episodes. More in-depth geochemical evaluations of both DST oils and inclusion oils, however, are required to resolve the question of one stage versus two stages of oil migration at the Mukluk area.

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the claims.

What is claimed is:

1. A method for determining the characteristics of oil in microquantity by ultraviolet fluorescence microspectrophotometry comprising the steps of:
   (a) obtaining a sample containing at least one oil-bearing inclusion from one location and measuring its fluorescence spectra by microspectrphotometery within a desired wavelength range;
   (b) obtaining a sample of reservoir oil from a location where said reservoir oil was substantially derived from the same source rocks as was said at least one inclusion,
      (i) measuring the fluorescence spectra of said reservoir oil by microspectrophotometry via the wavelength range used in step (a),
      (ii) determining the quality of said reservoir oil; and
   (c) characterizing the quality of oil contained in said at least one inclusion based upon fluorescence-oil quality correlations obtained from analysis of said reservoir oil.

2. The method as recited in claim 1 where in step (b) said reservoir sample comprises produced reservoir oil, or drill stem test oil.

3. The method as recited in claim 1 where in step (a) said sample comprises rock outcrops, drill cuttings, or core samples.

4. The method as recited in claim 1 where in step (a) said wavelength range is from about 400 to about 700 nm.

5. The method as recited in claim 1 where in step (c) said oil quality for the at least one oil-bearing inclusion is characterized by its API gravity, aromatic-to-saturate ratio, asphaltene content, and sulfur.

6. The method as recited in claim 1 where oil inclusions are less than about 30 $\mu$m in diameter.

7. The method as recited in claim 1 where maturation and path of migration of the reservoir oil are delineated via fluorescence spectra.

8. A method for predicting the quality of oil contained in a petroleum basin or exploration play area where at least one-oil-bearing inclusion is used in combination with ultraviolet light fluorescence and microspectrophotometry comprising the steps of:
   (a) obtaining from a basin or area of exploration play, a sample containing at least one oil-bearing inclusion and thereafter measuring the fluorescence spectra of said at least one inclusion by microspectrophotometry within a desired wavelength range;
   (b) obtaining a sample of reservoir oil from a location where said reservoir oil was substantially derived from the same source rocks as was said at least one inclusion;
      (i) measuring the fluorescence spectra of said reservoir oil by microspectrophotometry via the wavelength range used instep (a),
      (ii) determining the quality of said reservoir oil;
   (c) characterizing the quality of oil contained in said at least one inclusion based upon fluorescence-oil quality correlations obtained from analysis of said reservoir oil; and
   (d) predicting the quality of oil in said basin or exploration play area from which said at least one inclusion sample was obtained.

9. The method as recited in claim 8 where in step (b) said reservoir oil comprises produced crude oil or drill stem test oil.

10. The method as recited in claim 8 where in step (a) said sample comprises a rock outcrop, drill cuttings, or a core sample.

11. The method as recited in claim 8 where in step (a) said wavelength range is from about 400 nm to about 700 nm.

12. The method as recited in claim 8 where in step (d) said oil quality is characterized by its API gravity, aromatic-to saturate ratio, asphaltene content, and sulfur.

13. The method as recited in claim 8 where oil inclusions are less than about 30 μm in diameter.

14. The method as recited in claim 8 where the maturation and path of migration of the reservoir oil are delineated by fluorescence spectra.

15. A method for predicting the quality of oil contained in a petroleum basin or exploration play area where at least one oil-bearing inclusion is used in combination with ultraviolet light fluorescence and microspectrophotometry comprising the steps of:
(a) obtaining a sample containing at least one oil-bearing inclusion from said basin or play area and measuring the fluorescence spectra by microspectrophotometry within a wavelength range of from about 400 to about 700 nm;
(b) obtaining a sample of reservoir oil from a location where said reservoir oil was substantially derived from the same source rocks as was said as least one inclusion;
  (i) measuring the fluorescence spectra of said reservoir oil by microsphectrophotometry via the wavelength range used in step (a),
  (ii) determining the API gravity, aromatic-to-saturate ratio, asphaltene and sulfur content of said reservoir oil;
(c) characterizing the quality of oil contained in said at least one inclusion based upon fluorescence-oil quality correlations obtained from analysis of said reservoir oil; and
(d) predicting the quality of oil in said basin or exploration play area from the characterization of the oil quality of said at least one inclusion.

16. The method as recited in claim 15 where in step (b) said sample comprises produced reservoir oil or a drill stem test oil.

17. The method as recited in claim 15 where in step (a) said oil-bearing sample comprises rock outcropings, drill cuttings, or core samples.

18. The method as recited in claim 15 where oil inclusions are less than about 30 μm in diameter.

19. The method as recited in claim 15 where the maturation and path of migration of the reservoir oil are delineated by fluorescence spectra.

20. The method as recited in claim 15 where said reservoir oil comprises an oil seep.

* * * * *

UNITED STATES PATENT AND TRADEMARK OFFICE
CERTIFICATE OF CORRECTION

PATENT NO. : 4,814,614

DATED : March 21, 1989

INVENTOR(S) : Tien-Fung Tsui

It is certified that error appears in the above-identified patent and that said Letters Patent is hereby corrected as shown below:

Column 1, line 9, after "petroleum" insert --basins--.

Column 1, line 66, "(μ/cc)" should read --(∿1 cc)--.

Column 5, line 1, "the" (second occurrence) should be --The--.

Column 8, line 7, "wa" should read --was--.

Column 9, line 57, "recorder" should read --recorded--.

Column 10, line 10, "microspectrphotometery" should read --microspectrophotometry--.

Column 12, line 4, "microsphectrophotometry" should read --microspectrophotometry--.

Signed and Sealed this

Nineteenth Day of June, 1990

Attest:

HARRY F. MANBECK, JR.

*Attesting Officer*      *Commissioner of Patents and Trademarks*